United States Patent
High et al.

(10) Patent No.: US 9,910,959 B2
(45) Date of Patent: Mar. 6, 2018

(54) ENTRY, STORAGE AND RETRIEVAL OF MEDICAL INFORMATION FROM A PHARMACY

(71) Applicant: Wal-Mart Stores, Inc., Bentonville, AR (US)

(72) Inventors: Donald R. High, Noel, MO (US); Nicholas D. Rone, Bella Vista, AR (US); Michael Dean Atchley, Springdale, AR (US)

(73) Assignee: WAL-MART STORES, INC., Bentonville, AR (US)

( * ) Notice: Subject to any disclaimer, the term of this patent is extended or adjusted under 35 U.S.C. 154(b) by 14 days.

(21) Appl. No.: 15/062,503

(22) Filed: Mar. 7, 2016

(65) Prior Publication Data
US 2016/0267309 A1 Sep. 15, 2016

Related U.S. Application Data

(60) Provisional application No. 62/132,734, filed on Mar. 13, 2015.

(51) Int. Cl.
*G06F 19/00* (2018.01)
(52) U.S. Cl.
CPC .................. *G06F 19/322* (2013.01)
(58) Field of Classification Search
USPC .................................................. 235/462.46
See application file for complete search history.

(56) References Cited

U.S. PATENT DOCUMENTS

| 5,842,976 A | 12/1998 | Williamson |
| 6,003,006 A | 12/1999 | Colella et al. |
| 7,032,026 B1 | 4/2006 | Biswas et al. |
| 7,630,908 B1 * | 12/2009 | Amrien ................. G06F 19/322 235/487 |

(Continued)

FOREIGN PATENT DOCUMENTS

| EP | 1025528 | 8/2008 |
| EP | 2489149 | 8/2012 |

(Continued)

OTHER PUBLICATIONS

"MedCoach Medication Reminder: version 1.8", iTunes.apple.com, Sep. 19, 2013, GreatCall, Inc., accessed on Dec. 22, 2016; 2 pages.

(Continued)

*Primary Examiner* — Michael G Lee
*Assistant Examiner* — David Tardif
(74) *Attorney, Agent, or Firm* — Schmeiser, Olsen & Watts LLP

(57) ABSTRACT

A system and method includes: a pharmacy server receiving a customer ID code to allow a customer wireless access to his medical data file stored on the server; the server receiving adherence confirmation data from the customer and storing the adherence confirmation data into the medical data file to confirm that the customer is taking a prescribed medicine according to directions; and the server receiving additional data from the customer and storing the additional data into the medical data file, whereby the customer is provided with wireless access to enter, edit and retrieve data to and from his medical data file.

15 Claims, 6 Drawing Sheets

(56) References Cited

U.S. PATENT DOCUMENTS

| | | | |
|---|---|---|---|
| 7,975,292 B2 | 7/2011 | Corella | |
| 8,005,688 B2 | 8/2011 | Coffman et al. | |
| 8,302,187 B1 | 10/2012 | Gupta et al. | |
| 8,392,220 B2 | 3/2013 | Knowlton et al. | |
| 2003/0105555 A1 | 6/2003 | Lunak et al. | |
| 2003/0140928 A1 | 7/2003 | Bui et al. | |
| 2006/0136272 A1 | 6/2006 | Rubsamen | |
| 2008/0030309 A1 | 2/2008 | Darrouzet | |
| 2008/0059242 A1 | 3/2008 | Stanford | |
| 2008/0313721 A1 | 12/2008 | Corella | |
| 2009/0192648 A1* | 7/2009 | Namineni | A61J 7/0481 700/231 |
| 2010/0324936 A1 | 12/2010 | Vishnubhatla et al. | |
| 2011/0015945 A1 | 1/2011 | Addy | |
| 2011/0066260 A1 | 3/2011 | Condurso et al. | |
| 2011/0180441 A1* | 7/2011 | Bach | G06F 19/322 206/459.5 |
| 2011/0184755 A1 | 7/2011 | Yamaga et al. | |
| 2011/0226651 A1 | 9/2011 | Patino | |
| 2012/0303388 A1 | 11/2012 | Vishnubhatla et al. | |
| 2013/0054271 A1 | 2/2013 | Langford et al. | |
| 2013/0253291 A1 | 9/2013 | Dixon et al. | |
| 2013/0304506 A1* | 11/2013 | Gallivan | G06F 19/3431 705/3 |
| 2014/0039672 A1 | 2/2014 | Niinisto et al. | |
| 2014/0039911 A1 | 2/2014 | Iyer | |
| 2014/0058561 A1 | 2/2014 | Rothschild | |
| 2014/0089011 A1 | 3/2014 | Fletcher | |
| 2014/0142979 A1 | 5/2014 | Mitsunaga | |
| 2014/0188502 A1 | 7/2014 | Defrank et al. | |
| 2014/0277705 A1 | 9/2014 | Czaja et al. | |
| 2014/0350720 A1 | 11/2014 | Lehmann et al. | |
| 2014/0350949 A1 | 11/2014 | Utech et al. | |

FOREIGN PATENT DOCUMENTS

| | | |
|---|---|---|
| JP | 2013168820 | 8/2013 |
| KR | 20130038319 | 4/2013 |
| WO | 2003098399 | 11/2003 |
| WO | 2014037850 | 3/2014 |
| WO | 2014159933 | 10/2014 |

OTHER PUBLICATIONS

"Scan", Clinicate.com, 2014, Clinicate, LLC, accessed on Dec. 22, 2014; 4 pages.

Wideman, Mary V., et al. "Barcode Medication Administration: Lessons Learned from an Intensive Care Unit Implementation", Advances in Patient Safety vol. 3, FDA.gov, Feb. 2005, accessed on Dec. 22, 2014; 16 pages.

"Walgreens—Android Apps on Google Play", Play.Google.com, Nov. 6, 2014, Walgreen Co., accessed on Dec. 19, 2014; 2 pages.

"Search the Lowest Drug Price", LowestMed.com, updated 2014, LowestMed, first accessed on Dec. 19, 2014, most recently accessed Mar. 4, 2016; 1 page.

"How GoodRx Works", GoodRx.com, 2014, GoodRx, Inc., accessed on Dec. 19, 2014; 3 pages.

Dolan, Brian, "Walgreens app adds pill reminders, Rx transfer", Mobihealthnews.com, Mar. 12, 2012, accessed on Feb. 3, 2015; 3 pages.

* cited by examiner

ENTRY, STORAGE AND RETRIEVAL OF MEDICAL INFORMATION FROM A PHARMACY

RELATED APPLICATIONS

This application claims priority to U.S. Provisional Application Ser. No. 62/132,734, filed on Mar. 13, 2015 entitled "Entry, Storage and Retrieval of Medical Information from a Pharmacy", the entirety of which is incorporated by reference herein.

FIELD OF THE INVENTION

A method and system herein relates generally to entering, storing and retrieving information of a pharmaceutical customer into a database stored at a pharmacy. More specifically the customer may access, update and retrieve his or her own medical data file from a computer system of a pharmacy.

BACKGROUND

A pharmacy may provide a web site that allows a customer to take certain actions such as to refill his or her prescriptions, view his orders, view a current order status and the customer's prescription history, set up automatic refills, and provide a medical expense report of his prescriptions. However, there are many limitations to what is available to the customer via the existing pharmacy web sites. For example, the customer does not have visibility into his medical information pertaining to his prescriptions and other information associated directly with his prescriptions as the web sites are primarily used for tracking orders. Additionally, a mobile app (i.e. a software application installed onto the customer's mobile device such as a smart phone or other wireless device) is limited to ordering refills and/or viewing the customer's order history.

Improvements are desired for the entry, storage and retrieval of medical information for a customer having a prescription at a pharmacy.

BRIEF SUMMARY OF EMBODIMENTS

A method for medical information entry, storage and retrieval includes the steps of: (1) receiving and filling a prescription of a medicine for a customer at a pharmacy by placing the medicine into a container and supplying to the customer the prescription container along with an ID code plus directions for taking the medicine, wherein the ID code is linked to a medical data file created and stored for the customer on a server for the pharmacy; (2) receiving, via wireless communications to the server, the ID code for authentication and access to the customer's medical data file; (3) receiving, via wireless communications to the server, adherence confirmation data including a time and date that the medicine is taken to confirm adherence of the customer taking the prescribed medicine according to the directions, and storing the adherence confirmation data into the customer's medical data file; and (4) receiving, via wireless communications to the server, additional data pertaining to the customer that is unavailable from the customer's medical data file, and storing the additional data into the medical data file.

A system for the entry, storage and retrieval of medical data for a customer of a pharmacy includes: (1) a server for providing computer services to the pharmacy for creating and storing a medical data file for the customer in a database on the server when a prescription for the customer is filled for a medicine into a container and supplying to the customer the prescription container along with and an ID code linked to the customer's medical data file and directions for taking the medicine; (2) a receiving unit to receive data via wireless communications over the Internet from a wireless device of the customer, the received data including the ID code to authenticate and establish communications between the customer's wireless device and the server, wherein the received data includes data to edit or update the customer's medical data file stored in the database of the server; (3) and a transmitting unit to transmit data via wireless communications over the Internet from the server to the customer's wireless device, the transmitted data including portions of the customer's medical data file.

The above and other aspects of various embodiments disclosed herein will become apparent in view of the following description, claims and drawings.

BRIEF DESCRIPTION OF THE SEVERAL VIEWS OF THE DRAWINGS

The accompanying drawings, in which like numerals indicate like structural elements and features in various figures, are not necessarily drawn to scale.

DETAILED DESCRIPTION

In the following description, specific details are set forth although it should be appreciated by one of ordinary skill in the art that the systems and methods can be practiced without at least some of the details.

Figure 1:
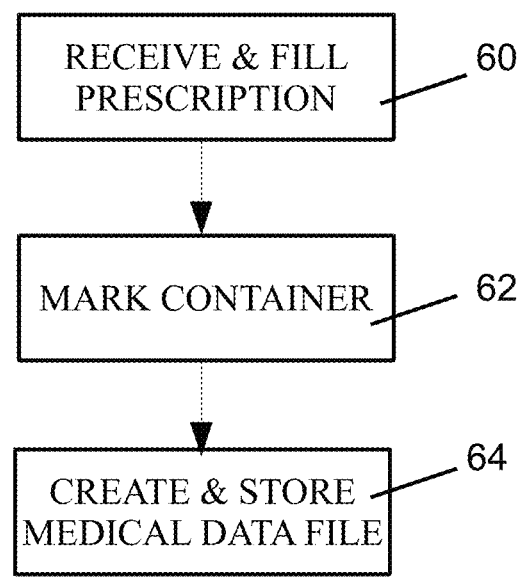
FIG. 1 is a flow chart diagram of a method for filling a medical prescription for a customer, and creating and storing a medical data file for the customer on a pharmacy computer.

In the flow chart diagram of FIG. 1 a method is shown for filling a medical prescription for a customer and creating and storing a medical data file. When filling a prescription for a medicine a pharmacist places the prescribed medicine into a bottle or container as indicated in block 60. Of course the medicine could be in pill form, liquid form, in a syringe, or in any other form as prescribed by a doctor. The prescription could also be directed towards any sort of medical device prescribed by a doctor and available from a pharmacy. When filling the prescription the pharmacist assigns a customer ID code to a new customer. If the customer is an existing customer, then the same customer ID code can be used for all prescription data for the customer at the pharmacy. Alternately, a separate ID code could be assigned to each prescription.

In block 62 the customer ID code is printed or otherwise marked or added to the container, to a label on the container, or onto an attached document such as instructions for taking the medicine. The primary purpose of the ID code is to link and uniquely identify the filled prescription of a customer to the customer's medical data file stored on a server for a pharmacy.

The customer's medical data file is originally set up by the pharmacist and includes information such as: the customer's name, telephone number, email and postal address; the name and dosage of the prescribed medicine; instructions for taking the medicine including one or more predetermined tolerances for taking the medicine; and, a name and contact information of a doctor who prescribed the medicine. Eventually, the customer's medical data file will be appended to include other information such as: the customer's compliance determination data which is a recordation of whether the customer is taking the medicine properly according to the instructions; and, the customer's prescription medicine history including compliance determination data for taking previously prescribed medicines.

Turning back to FIG. 1, block 62, the ID code and the label for the container are printed at the same time to ensure that the correct code is attached to, or otherwise accompanying, the container for each individual prescription. Any type of ID code can be used that can be accessed by way of any known method, such as but not limited to, a scannable barcode, a QR code, a magnetic strip code, an OCR (optical character recognition code), an encrypted code, standard alpha-numerical characters, a code identifiable by digital imaging, or any other code. A label marking device, such as a printer or dedicated label marking machine, can be used to mark the ID code and directions onto the container, onto a label to be affixed to the container, or onto a separate piece of paper accompanying the container of medicine.

The ID code can be a set of alpha-numerical characters that can be read by the customer, or preferably it is an encrypted machine readable code. For example, an ID code can be a QR code which is a type of matrix barcode or two dimensional barcode consisting of an array of black and white squares, typically used for storing URLs or other information to be read by a camera on a smartphone.

One example of a machine code-reading device is a barcode reader or scanner which is an electronic device for reading printed barcodes such as a barcode or QR code from the label of the container. The barcode reader consists of a light source, a lens and a light sensor for translating optical impulses into electrical pulses.

If the prescription being filled is for a new customer, then a new medical data file is created and stored in a database on the pharmacy computer/server as shown in FIG. 1, block 64. If a medical data file for the customer already exists in the database, then the new prescription data is added to the customer's existing medical data file. The pharmacist can also set up login information for a new customer such as an user name and password to allow the customer, after the prescription is filled, to be able to login at a pharmacy website which is available on the Internet. Alternately, the customer could use his assigned ID code along with his name and/or other identifying data on the pharmacy website to create a new account and select an user name and password. The ID code thereafter allows the customer access to his or her medical data file anytime by wireless communications over the Internet.

The medical data files of prescription records for pharmacy customers can be stored (as shown for example in FIG. 5) in a database 126 located on a server 120 located at the pharmacy, or they can be accessed and stored on a remote server by wireless communications over the Internet 140. The remote server can be located, for example, in a separate room of the pharmacy, at a separate location servicing the pharmacy, at a store headquarters, or any other location.

Figure 5:
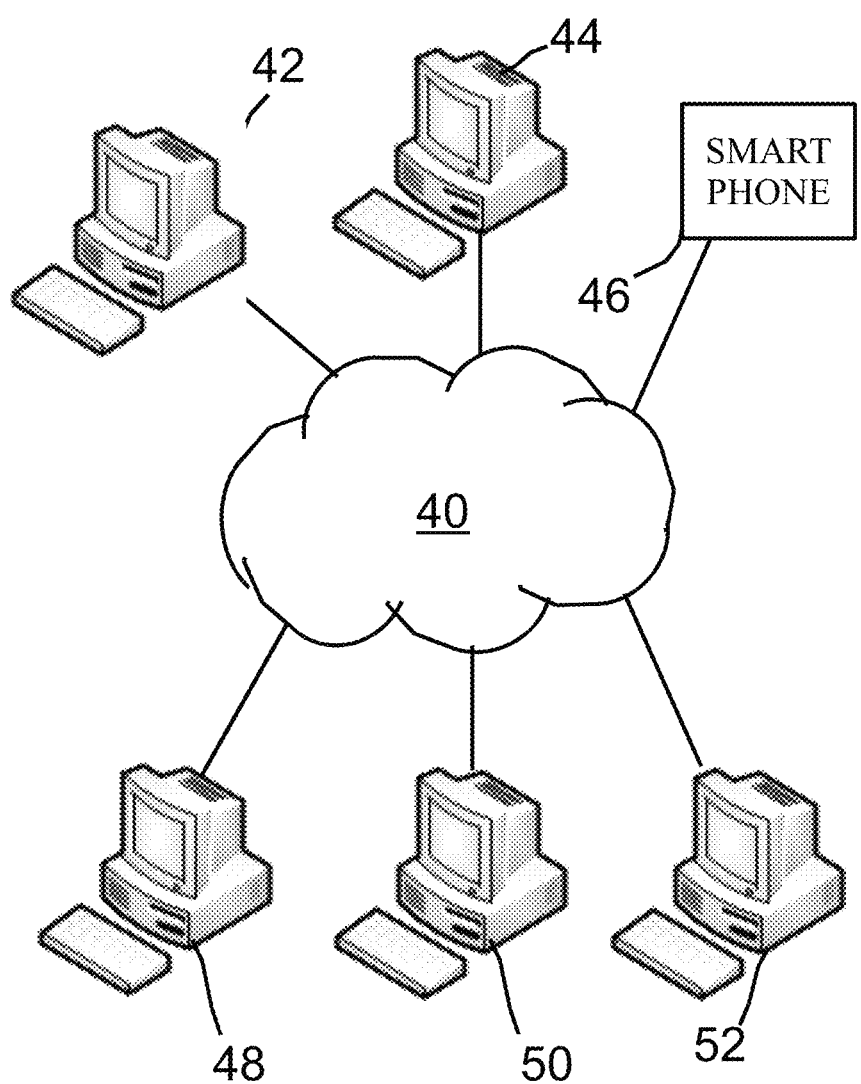
FIG. 5 is a diagrammatic representation of a wireless communications system architecture.

When the pharmacist receives a prescription from a new customer, the pharmacist will enter the customer's personal information such as (but not limited to) his or her name, address and phone number which is input from a pharmacist's workstation 132 into the pharmacy's computer system 120 (FIG. 5). A software application resident on the pharmacy's server will present an user interface (not shown) on the pharmacist's workstation 132 so that the pharmacist can enter and retrieve data from the pharmacy server 120. The software application will assign an unique customer ID code to the customer and will create an unique medical data file 130 in the database 126 for the customer which is accessible via the customer's ID code. Other security codes and measures can be implemented to further secure the customer's medical data file and if the customer loses the ID code, then the pharmacist can access the customer's medical data file using the customer's personal information such as his name, telephone number, or social security number. In addition to the customer's personal information, the pharmacist can enter other information in predetermined entry fields mapped to the customer's medical data file 130 such as information identifying the customer's prescribed medicine, dosage, and the name of the doctor who is prescribing the medication. The medicine is typically prescribed for a specific time period and a specific number of refills, such as 30 pills to be refilled once a month for a period of one year.

For each medicine prescribed to a customer, the customer receives instructions for taking the medicine which includes guidelines and tolerances, set by the customer's doctor, for proper care, usage and administration of the medicine. The tolerance levels are preset margins of error that are acceptable for proper administration of the medicine such as setting a window of time for when to take the medication for maximum effectiveness. Other guidelines can include the dosage of the medicine which can be adjusted by the number of pills or spoonfuls of liquid medicine taken at one time, whether to take the medicine with food or water, etc. The guidelines and tolerances are all predetermined by the doctor according to the specific needs of the customer for whom the medicine is prescribed.

For example, a prescription may be filled for a customer who is required to take one pill twice a day, once in the morning after breakfast and the second time in the early evening after a meal. Let us assume that the effectiveness of the medicine is maximized if the pills are taken at 12 hour intervals and the pills are still relatively effective if taken within 8 to 14 hours of one another. Also, let's assume that damage to the customer's stomach lining could occur if the medicine is not taken immediately after or during a meal. In this case, the tolerances could be set to taking one pill in the morning during or immediately after breakfast between 7-10 am, and one pill in the evening during or immediately after dinner between 7-10 pm.

When the customer is taking the medicine either he, or a caregiver responsible for overseeing that the customer takes the medicine, can access the customer's medical data file on the pharmacy server using wireless communications. Of course only the customer can have access to the pharmacy server and his medical data file which is secured by the customer's ID code as well as standard security measures including an user name and password. When the customer logs on to the pharmacy server the first time, he can be asked to register his wireless device as an additional security measure by allowing the pharmacy server to receive the Internet Protocol (IP) address of the wireless device. Thereafter, only communications received from the customer's registered wireless device will be allowed access to the server or the customer's medical data file.

If the customer is unable to communicate via a wireless device, then an authorized caregiver (such as a nurse or a spouse) can be granted permission to access the customer's medical data file in order to submit adherence confirmation data to taking the medicine. The adherence confirmation data can also be referred to as compliance confirmation data or compliance determination data. Any type of known wireless communications device can be used to communicate over the Internet, such as but not limited to a smart phone, a tablet, a desktop computer, a laptop computer, etc. After taking his/her medicine, the customer or his authorized caregiver can log onto the pharmacy server and access the customer's medical data file using the customer's ID code.

Figure 2:
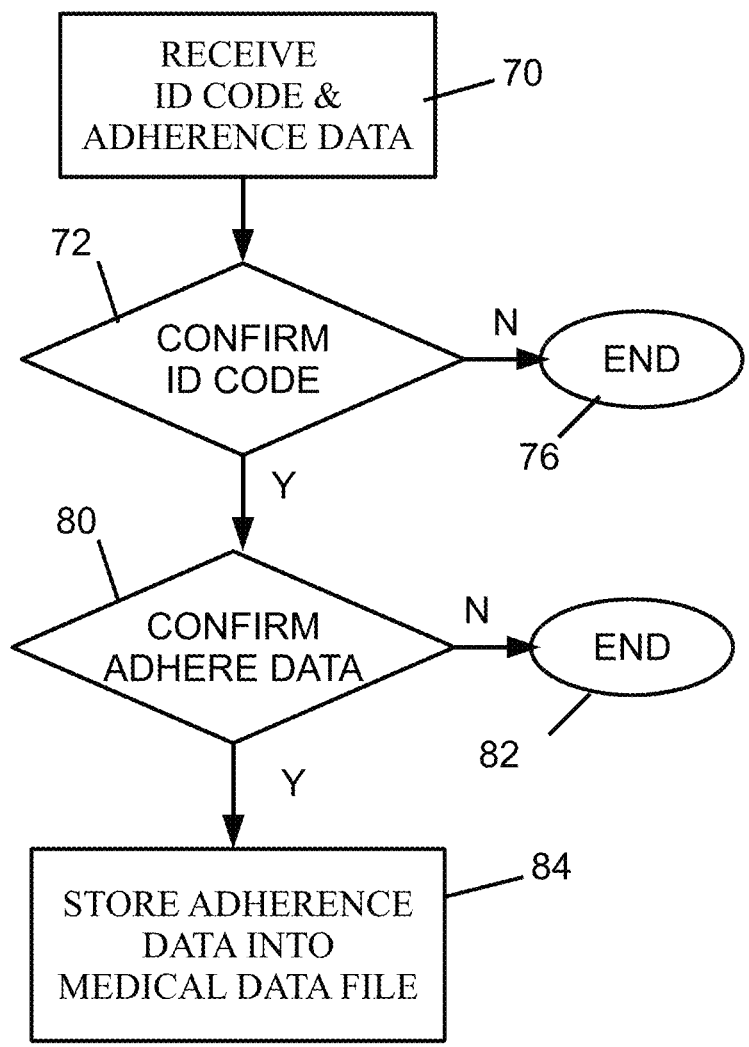
FIG. 2 is a flow chart diagram of a method of receiving a customer's adherence confirmation data to confirm that a customer has properly taken his or her medicine.

FIG. 2 is a flow chart diagram of a method of receiving adherence confirmation data to verify that the customer is taking the prescribed medicine according to the instructions. When the customer is taking the medicine either he, or a caregiver responsible for overseeing that the customer takes the medicine, can access the customer's medical data file on the pharmacy server using wireless communications. Of course only the customer can have access to the pharmacy server and his medical data file which is secured by the customer's ID code as well as standard security measures including an user name and password. However if the customer is unable to communicate via a wireless device, then an authorized caregiver (such as a nurse or a spouse) could be granted permission to access the customer's medical data file in order to submit adherence confirmation data to taking the medicine. Any type of known wireless communications device can be used to communicate over the Internet, such as but not limited to a smart phone, a tablet, a desktop computer, a laptop computer, etc.

After taking his/her medicine, the customer or his authorized caregiver can log onto the pharmacy server and access the customer's medical data file using the customer's ID code. A single ID code could be provided to the customer for all of his prescriptions, or a separate ID code could be provided to the customer for each separate prescription. In either alternative, the customer's ID code(s) allow online access to the customer's medical data file.

The ID code and adherence confirmation data to be added to the customer's medical data file is received by the pharmacy server as shown in FIG. 2 block 70. A determination is made in decision block 72 whether the ID code received online by the customer is valid. In other words, a determination is made whether the received ID code corresponds with other received authentication information such as the customer's name, address or social security number. If the ID code is determined to be invalid or incorrect in decision block 72, then the process ends in block 76. If the ID code is verified in block 72, then access is allowed to the customer's medical data file. The adherence confirmation data can either accompany the ID code, or preferably be entered and received from the customer's wireless device and thereafter submitted after permission is granted to access the customer's data file. The customer can then send the adherence confirmation data by filling in required data entry fields of an adherence confirmation interface to include information such as the time and date that the medicine was taken, the dosage taken, the name of the medicine taken, and/or any other required adherence confirmation data as required for the specific prescription.

The adherence confirmation interface can run as an app (i.e. a software application) from a shell program on the customer's wireless device. The application can request or even require a second confirmation such as by e-signature from a second party such as a caregiver, spouse, or other person who witnesses that the customer took his medication as reported to the pharmacy.

The pharmacy server checks, as shown in decision block 72 of FIG. 2, whether the ID code has been received from the customer's wireless device. If NO, then the process ends in block 76. If YES, then the customer's medical data file is opened and the process continues to decision block 80 where it is determined whether the adherence confirmation data has been received from the customer's wireless device. If the answer is NO, then the process will end in block 82. If the answer is YES, then the adherence confirmation data is stored in the customer's medical data file as shown in block 84.

In the above example, the time and date entered by the customer or caregiver to indicate when the medicine was taken is considered as the adherence confirmation data. However, the adherence confirmation data can be set and defined by the customer's doctor for confirming that the medicine is properly taken by the customer according to the instructions accompanying the prescription, and could include information such as, but not limited to, (1) the time at which the medicine is taken, (2) the dosage of the medicine taken, (3) the number of pills taken, (4) whether the medicine was taken with food or drink, (5) a dual confirmation by both the customer and another person such as the caregiver of the information reported to the pharmacy server, and (6) whether the prescribed medicine was taken simultaneously with other medicine, etc.

FIG. 5 illustrates a typical wireless network whereby computers 42, 44, 48, 50 and 52 and a smart phone 46 or any other wireless device can communicate wirelessly with one another over the Internet network 40. In this example, the customer could use the smart phone 46 to communicate with the pharmacy server 48 via the Internet 40 to access the customer's medical data file resident on the pharmacy server.

Figure 6:
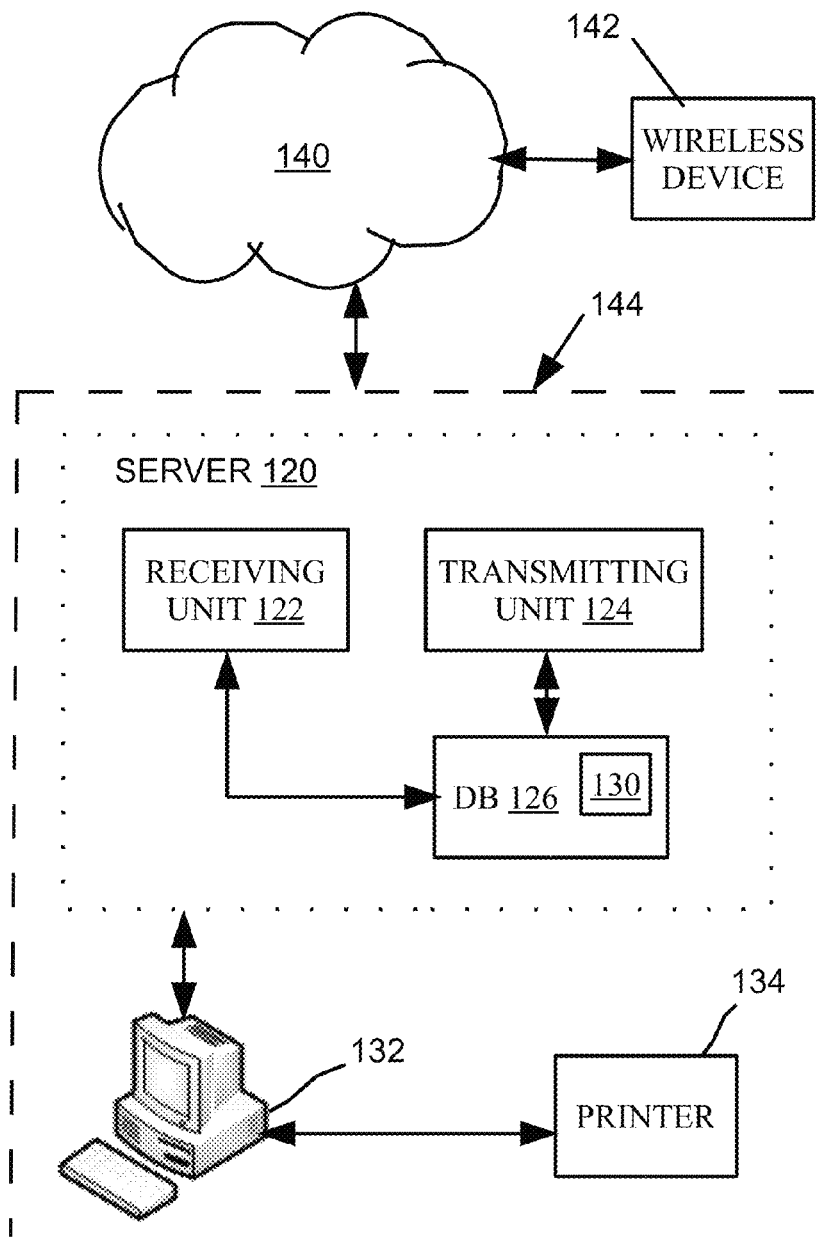
FIG. 6 is an alternative diagrammatic representation of an architecture of a wireless communications system.

An alternative structural diagram of the architecture of a wireless communications system that can be utilized is shown in FIG. 6. Here a wireless device 142 such as a customer's smart phone communicates with the pharmacy's system 144 via the Internet depicted here as cloud 140. The pharmacy system 144 includes a server 120 connected to one or more pharmacist work stations 132 whereby each station typically includes a computer monitor, keyboard and mouse (not shown) which are further connected to a printer 134. The printer 134 can include the capabilities of printing a label which can thereafter be affixed to the prescription container, whereby the label could include information such as, but not limited to, directions for taking the medicine, the name of the medicine, the date of filling the prescription, an expiration date, dosages, the number of pills in the container, the name, address and phone number of the customer and the pharmacy, and the ID code. The printer could also print out a separate sheet of directions for taking the medicine, along with the ID code.

The pharmacy server 120 includes a receiving unit 122, a transmitting unit 124 and a database 126. The customer's medical data file 130 is stored in the server's database 126 which in turn is accessible by both the receiving unit 122 and the transmitting unit 124. The receiving unit 122 is equipped to receive data via wireless communications over the Internet from a wireless device 142 such as the customer's smart phone, whereby the received data includes the ID code to authenticate and establish communications between the wireless device 142 and the server 120. The received data can also include data to edit or add to the customer's medical data file 130. The transmitting unit 124 is equipped to send data via wireless communications over the Internet from the server to the wireless device 142, whereby the transmitted data can include portions of the customer's medical data file 130.

In FIG. 6, the customer or caregiver uses his smart phone 142 or another wireless device to connect over the Internet 140 to the pharmacy server 120 by providing authentication data to the server 120 by way of a security code, password or other known verification method. Once authenticated and connected to the pharmacy server, the customer or caregiver must either scan and send the ID code from the container, or manually or otherwise enter the ID code to be sent from the smart phone 142 to the pharmacy server 120 to allow access to the customer's medical data file 130.

The pharmacy customer can input information into his medical data file that is not otherwise available from his healthcare provider, doctor, insurance company or any other source. The customer can build and have access to a more complete medical data file by adding historical data that is personal to him on topics such as, but not limited to, medical and mental health, the medical and mental health history of his blood relatives, prescribed medications and treatments, non-prescription drugs, vitamins, holistic medicines, chiropractic treatment, acupuncture treatment, homeopathic treatment, alternative medical treatments, allergies, hospitalization, stress related events (e.g. deaths in the family, job changes, etc.), sleep habits, weight variations, rehabilitation visits, heart rates, blood pressures, travel information, exercise information, blood sugar measurements, toothaches and other dental issues, vision issues, consumption of alcohol and tobacco, etc.

Figure 3:
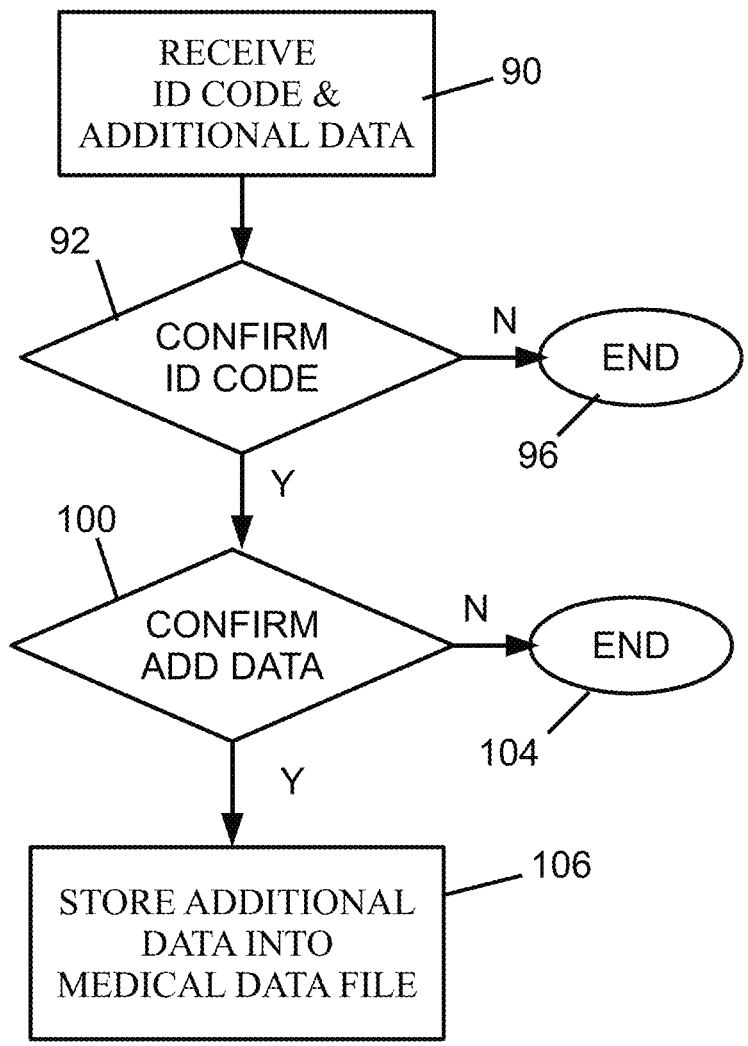
FIG. 3 is a flow chart diagram of a method of receiving additional customer data.

If the customer wishes to update his or her existing pharmacy medical data file, he or she may do so in accordance with the steps outlined in FIG. 3. The ID code is received in block 90 at the pharmacy server from the customer's wireless device and the ID code is either verified or denied in decision block 92. If the ID code is denied in decision block 92, then the process ends in block 96. If the ID code is confirmed in decision block 92, then the pharmacy server allows access to the customer's medical data file located in a database on the pharmacy server. Decision block 100 determines whether additional data has been submitted and received from the customer's wireless device. If NO, then the process ends in block 104. If YES, then the additional data is added to the customer's medical data file in block 106.

Figure 4:
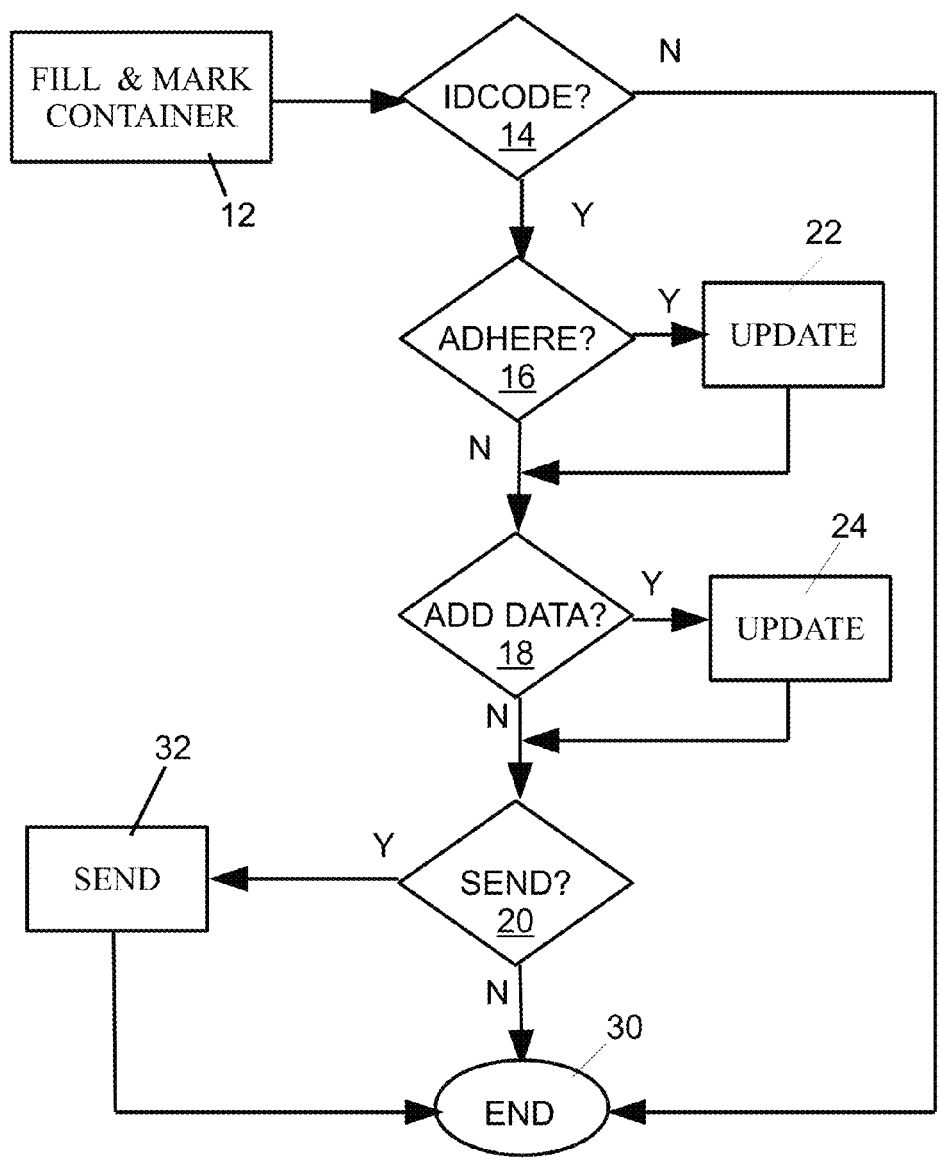
FIG. 4 is a flow chart diagram of an embodiment of a method for a pharmacy computer system to enter, store, modify and send out data relating to a customer's medical data file.

FIG. 4 is a flow chart diagram of an embodiment of a method for a pharmacy computer system to enter, store, modify and send data relating to a customer's medical data file. In block 12 the prescription is received and filled by the pharmacist into a container which is marked with an ID code that is unique for the customer. A medical data file linked to the ID code is created and stored into a database of the pharmacy server. The customer is also provided with an user name and password to access the pharmacy server by the pharmacist. Alternately, the customer can go to the pharmacy URL on the Internet and enter his ID code in order to set up his pharmacy on-line account which allows him to set his own user name and password.

After the customer receives his/her medicine, he/she has the option of accessing the pharmacy server and his medical data file via wireless communications over the Internet. Upon accessing the pharmacy URL, the customer will enter his user name and password in order to logon to the pharmacy website. After login on to the pharmacy website, the pharmacy online interface prompts the customer for his unique ID code. Decision block 14 determines whether a valid ID code is received by the pharmacy server which corresponds with the customer's logon information (e.g. user name and password). If the ID code is not valid, then access to any of the pharmacy data files is denied and the process ends in block 30. If the ID code is valid, then the customer is allowed access to his medical data file and the process continues to block 16.

Once the customer has been allowed access to his medical data file, he has options to take several different actions. An entry field on the user interface queries whether the customer wishes to submit adherence confirmation data, as in decision block 16, to confirm that he is taking the medicine according to the directions as prescribed. If he answers the query in the negative, then the process moves to block 18. If he answers the query in the affirmative, then he will be prompted to enter adherence confirmation data into the proper entry fields and the customer's medical data file will be updated as shown in block 22 with the adherence confirmation data received from the customer and saved into the pharmacy database. Thereafter, the method will continue in decision block 18.

Decision block 18 determines if the customer wishes to submit additional data to his medical data file, or if he wishes to edit existing information in his medical data file. This additional data includes, but is not limited to, the customer's medical and mental health, his past medical and mental health history, the medical and mental health history of his blood relatives, his past list of prescribed medications and treatments, his non-prescription drug history including vitamins and holistic medicines, any chiropractic treatment history, any acupuncture treatment history, his homeopathic treatments, his alternative medical treatments and practices, his allergies, his hospitalization history, etc.

If the customer completes an entry field to indicate that he wishes to submit additional information to his medical data file at the pharmacy, or he wishes to make changes to the information in the data file, then decision block 18 is answered in the affirmative and the customer's medical data file is appended, edited or otherwise updated in block 24. After the update, the process moves on to block 20. If the decision block 18 is answered in the negative, then the process goes immediately to block 20.

The user interface which allows the customer to add data into the customer's medical data file at the pharmacy can also include entry fields whereby the customer can create new entries into the medical data file which did not previously exist. For instance, let us assume that the default medical data file setup does not include an entry for insomnia. The customer may wish to add an insomnia field where he can indicate that he occasionally suffers from insomnia. He could also add a possible insomnia causation field where he can include information such as his observation that, over a 6 month period of time, the insomnia only occurs when he drinks an alcoholic beverage within 4 hours of going to bed.

Returning to FIG. 4, in decision block 20 the customer is queried whether he wishes to receive a copy of his medical data file. If the answer is NO, then the process ends in block 30. If the answer is YES, then the customer's medical data file is sent wirelessly via the Internet from the pharmacy server to the customer's wireless device as shown in block 32. Block 32 can also include an option for the customer to select to have a hard copy of his medical data file mailed to him via U.S. postal mail. The customer could also choose to have only a selected portion of his medical data file sent to him. Furthermore, the customer could choose to have a portion or the full medical data file sent via wireless communications, or regular postal mail, to his doctor, clinic or other destination.

A report application can also be made available on the pharmacy server to allow access by the customer to receive or send a report which could include information such as the history of the customer's compliance in taking his medicine. The report could be presented in any convenient format, such as in a graphical or tabular form, and could include historical customer information including the customer's compliance determination data, dates of reported compliance or non-compliance, etc. The report could also be used to provide an analysis of the customer's medical data file that could be sent via wireless communications (or as written reports via postal mail) to one or more of the customer, a pharmacist, a doctor, a nurse, a caregiver, an insurance company, a hospital or others involved in the prescribing, distributing, maintaining, monitoring and administering of the prescription medicines of the customer. The above report(s) could be automatically scheduled to run at predetermined time intervals such as once a month via a software program on the server, or the report program could be manually selected and run by the customer.

Notifications regarding the prescribed medicine can be sent at any time as emails via wireless communications from the server (or by postal mail) to one or more of the customer, a pharmacist, a doctor, a nurse, a caregiver, an insurance company, a hospital or others involved in the prescribing, distributing, maintaining, monitoring and administering of the medicine to the customer. The notifications can be automatic alerts occurring at predetermined intervals such as once a month and the notifications can include, but are not limited to, reminders for the customer to take his medicine, that the prescription medicine is about to expire, or to contact the pharmacy for a refill. The notifications can also be sent manually by a pharmacist from the pharmacy.

While specific embodiments have been shown and described, it should be understood by those skilled in the art that various changes in form and detail may be made therein.

What is claimed is:

1. A medical information entry, storage and retrieval method comprising the steps of:
   receiving and filling a prescription of a medicine for a customer at a pharmacy by placing the medicine into a container and supplying to the customer the prescription container along with an ID code and directions for taking the medicine, wherein the ID code is linked to a medical data file created and stored for the customer on a server for the pharmacy and allows access to, and modification of, the medical data file by the customer;
   receiving, via wireless communications to the server, the ID code for authentication and access to the customer's medical data file;
   receiving, via wireless communications to the server, adherence confirmation data including a time and date that the medicine is taken to confirm adherence of the customer taking the prescribed medicine according to the directions, and modifying the customer's medical data file by storing the adherence confirmation data into the customer's medical data file; and
   receiving, via wireless communications to the server, additional data pertaining to the customer that is unavailable from the customer's medical data file, and further modifying the customer's medical data file by storing the additional data into the medical data file at the server for the pharmacy for subsequent access of at least one of the modified medical data file or the further modified medical data file by the ID code.

2. The medical information entry, storage and retrieval method of claim 1, wherein the step of receiving additional data comprises confirmation that the additional data was received from the customer.

3. The medical information entry, storage and retrieval method of claim 1, wherein the step of receiving additional data comprises confirmation that the additional data was received from a doctor, a nurse, a caregiver, a pharmacist or others involved in prescribing, distributing, maintaining, monitoring or administering the medicine to the customer.

4. The medical information entry, storage and retrieval method of claim 1, further comprising the steps of:
   receiving a request at the server for a copy of the medical data file;
   confirming that the request was received from the customer; and
   sending the copy of the medical data file to the customer via wireless communications.

5. The medical information entry, storage and retrieval method of claim 1, further comprising:
   receiving a request at the server for a copy of the medical data file;
   confirming that the request was received from an authorized user being a doctor, a nurse, a caregiver, a pharmacist or another person involved in prescribing, distributing, maintaining, monitoring and administering the medicine to the customer; and
   sending the copy of the medical data file to the authorized user via wireless communications.

6. The medical information entry, storage and retrieval method of claim 1, further comprising the step of providing a report via wireless communications of customer adherence to taking the medicine according to the directions, wherein the report is provided from the server to one or more of the customer, a doctor, a nurse, a caregiver, or another person involved in prescribing, distributing, maintaining, monitoring and administering the medicine to the customer.

7. The medical information entry, storage and retrieval method of claim 1, wherein the additional data comprises data for tracking symptoms of a medical condition of the customer, data of the customer's medical history, prescription cost information, data of medical history of the customer's blood relatives, a list of the customer's prior prescription medicines, adherence confirmation data of taking medicines according to supplied instructions, data tracking the customer's consumption of alcohol and tobacco, data tracking the customer's food and beverage intakes, data tracking the customer's blood pressure, data tracking the customer's blood sugar levels, data tracking the customer's non-prescription medicines and vitamins and adherence to taking the non-prescription medicines and vitamins, and data tracking a number of pills remaining in the container.

8. The medical information entry, storage and retrieval method of claim 1, wherein the ID code is a machine readable bar code.

9. The medical information entry, storage and retrieval method of claim 1, further comprising marking the ID code onto the container, onto a label to be affixed to the container, or onto the directions.

10. The medical information entry, storage and retrieval method of claim 1, wherein notifications regarding the prescribed medicine are sent from the server to one or more of the customer, a pharmacist, a doctor, a nurse, a caregiver, an insurance company, a hospital or others involved in the prescribing, distributing, maintaining, monitoring and administering of the medicine to the customer.

11. A system for the entry, storage and retrieval of medical data for a customer of a pharmacy, comprising:
- a server for providing computer services to the pharmacy for creating and storing a medical data file for the customer in a database on the server when a prescription for the customer is filled for a medicine into a container and supplying to the customer the prescription container along with an ID code linked to the customer's medical data file and directions for taking the medicine, the linked ID code allowing access to, and modification of, the medical data file by the customer to the medical data file;
- a receiving unit connected to the server to receive data via wireless communications over the Internet from a wireless device of the customer, the received data including the ID code to authenticate and establish communications between the customer's wireless device and the server, wherein the received data includes data to edit or update the customer's medical data file stored in the database of the server, the edited or updated customer medical file accessible by the ID code; and
- a transmitting unit connected to the server to transmit data via wireless communications over the Internet from the server to the customer's wireless device, the transmitted data including portions of the customer's medical data file.

12. The system of claim 11 for the entry, storage and retrieval of medical data for a customer of a pharmacy, wherein the received data further comprises data of adherence of the customer taking the prescribed medicine according to the directions.

13. The system of claim 11 for the entry, storage and retrieval of medical data for a customer of a pharmacy, wherein the customer's wireless device is a smart phone, a desktop computer, a laptop computer, a computer tablet or pad, or another mobile wireless device.

14. The system of claim 11 for the entry, storage and retrieval of medical data for a customer of a pharmacy, further comprising a label marking device for marking the directions onto the container, onto a label to be affixed to the container, or onto a separate paper accompanying the container of medicine.

15. The system of claim 11 wherein the server further comprises a report application to analyze the medical data file including the compliance determination data and to send a report to one or more of the customer, a pharmacist, a doctor, a nurse, a caregiver, an insurance company, a hospital or others involved in the prescribing, distributing, maintaining, monitoring and administering of the medicine to the customer.

* * * * *